United States Patent [19]

Wallace

[11] Patent Number: 5,036,840
[45] Date of Patent: Aug. 6, 1991

[54] NEBULIZER SYSTEM

[75] Inventor: Dean R. Wallace, Fort Myers, Fla.

[73] Assignee: Intertech Resources Inc., Lincolnshire, Ill.

[21] Appl. No.: 541,066

[22] Filed: Jun. 20, 1990

[51] Int. Cl.⁵ ............................................ A61M 11/00
[52] U.S. Cl. ........................... 128/200.21; 128/203.12
[58] Field of Search ...................... 128/203.12, 200.14, 128/200.21, 204.18, 205.12, 205.27, 911, 912, 203.28, 205.13

[56] References Cited

U.S. PATENT DOCUMENTS

| | | | |
|---|---|---|---|
| 4,360,018 | 11/1982 | Choksi | 128/205.12 |
| 4,463,755 | 8/1984 | Suzuki | 128/204.18 |
| 4,823,784 | 4/1989 | Bordoni et al. | 128/200.16 |

Primary Examiner—Clifford D. Crowder
Assistant Examiner—Stephen R. Funk
Attorney, Agent, or Firm—Marshall, O'Toole, Gerstein, Murray & Bicknell

[57] ABSTRACT

Respiratory apparatus comprising a member forming first, second and third connected gas flow passages. A patient device is connected to the third passage for conducting gas flow to and from a patient. First and second gas flow tubes are connected to the first and second passages for conducting gas to and from the third passage and the patient. A nebulizer is attached to the center of the member for feeding aerosolized medicine into the passages of the member and the tubes, for inspiration by the patient. Further, filters are mounted in both of the flow tubes for filtering makeup air and expired gas, the filters futher serving to control the gas flow through the tubes. The filters may have the same weight (and therefore the same air flow resistance), or the filter of one of the tubes may have less weight than the filter of the other tube.

11 Claims, 1 Drawing Sheet

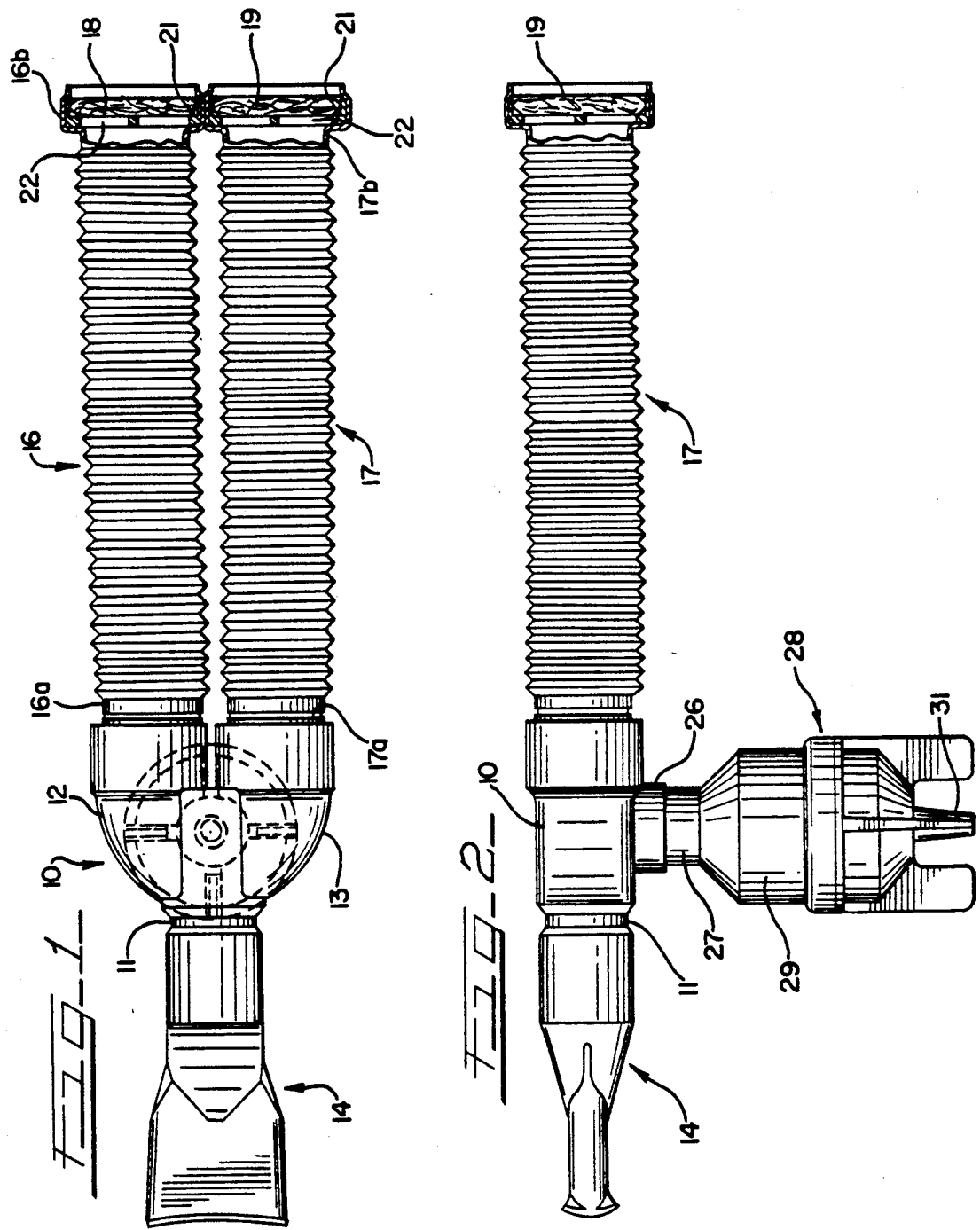

NEBULIZER SYSTEM

FIELD AND BACKGROUND OF THE INVENTION

This invention relates to apparatus for delivering medicine to the respiratory system of a patient, and more particularly to an improved hand-held nebulizer system.

Respiratory care devices are known and in widespread use for delivering medicine directly to the respiratory system, thereby maximizing the effectiveness of the medicine. In a typical device of this nature, a stream of gas (which may be ordinary air) is passed through a nebulizer containing the medicine. The medicine is aerosolized and mixed with the gas stream in the nebulizer, and the gas medicine mixture is then inhaled by the patient, causing the mist or fine particles of the medicine to be distributed in the respiratory system of the patient. This is, for example, a common method of administering aerosolized medication to a patient in respiratory distress.

Prior art devices include the "Respirgard II TM Nebulizer System" marketed by Marquest Medical Company. In this device a mouthpiece is fastened to the center leg of a wye; one of the other two legs is connected to a nebulizer and the third leg is connected to an exhaust filter. Valves are also provided to cause inspiration through the nebulizer leg and expiration through the filter leg.

The Hudson RCI company markets a device referred to as the "ISO-NEB TM system" which is similar in principle to the Respirgard II Nebulizer System except that the ISO-NEB system includes a T coupling instead of a wye.

It is believed that all prior art devices of this general nature include one-way check valves for controlling the direction of gas flow to cause inspiration through the nebulizer and expiration through the filter. The provision of valves is, however, disadvantageous because it adds expense and weight to the unit. Further, valves have a resistance to air flow which could result in excessive inspiratory effort on the part of sick patients.

It is a general object of the present invention to provide an improved apparatus which avoids the above disadvantages and has other important advantages.

SUMMARY OF THE INVENTION

Respiratory apparatus in accordance with this invention comprises a member forming first, second and third connected gas flow passages. A patient device is connected to the third passage for conducting gas flow to and from a patient. First and second gas flow tubes are connected to the first and second passages for conducting gas to and from the third passage and the patient. A nebulizer is attached to a fourth passage formed in the member for feeding aerosolized medicine into the passages of the member and the tubes, for inspiration by the patient. Further, filters are mounted in both of the flow tubes for filtering makeup air and expired gas, the filters further serving to control the gas flow through the tubes. In one form of the invention the filters have the same weight (and therefore the same air flow resistance), and in another form of the invention the filter of one of the tubes has less weight than the filter of the other tube.

BRIEF DESCRIPTION OF THE DRAWINGS

The invention will be better understood from the following detailed description taken in conjunction with the accompanying figures of the drawings, wherein:

FIG. 1 is a plan view of apparatus incorporating the invention; and

FIG. 2 is a side view of the apparatus.

DETAILED DESCRIPTION OF THE DRAWINGS

With reference to the drawings, a preferred embodiment of the apparatus comprises a straight wye 10 including a center leg 11 and two side-by-side legs 12 and 13. In the specific example shown in the drawing, the three legs are parallel and they form three interconnected flow passages within them.

Attached to the center leg 11 is a device 14 for conducting gas flow to and from a patient (not shown). In this example, the device 14 comprises a mouthpiece which has a tight fit with the leg 11.

Connected to the other two legs 12 and 13 are two corrugated plastic gas flow tubes 16 and 17, respectively. One end 16a and 17a of each tube is connected to the legs 12 and 13, and the opposite ends 16b and 17b have mounted therein filters 18 and 19. Each of the filters is disc shaped and is mounted in an annular housing 21. Each housing may also include a spider or cross member 22 on its interior side to support the filter. The housings 21 are secured in place in the tubes 16 and 17 by, for example, flaring the ends 16b and 17b outwardly slightly and folding them around the outer sides of the housings.

The filters may be a commonly used type found in respiratory care products, which block the flow of bacteria, virus and medicine. A filter marketed by 3M Corp. under the trademark Filtrete filter may be used. In the prefered embodiment of the invention, the two filters 18 and 19 have the same weight.

Also formed on the wye 10 is a coupling 26 which is secured to the outlet 27 of a nebulizer 28 that may have a conventional design. The coupling 26 is located at the center of the wye, midway between the two legs 12 and 13. In addition to the outlet 27, the nebulizer 28 includes a housing 29 which forms a container for medicine, an atomizer within the housing 29, and a gas inlet 31. The inlet is connected by a tube (not shown) to a source of gas, the gas flows through the atomizer, and the gas-medicine mixture flows through the outlet and into the three passages of the wye 10.

As a specific example of the construction and use of the apparatus, the thin-walled plastic tubes 16 and 17 are each about six inches in length and have an I.D. of about one inch. Each of the two filters has a weight of about 250 grams/square meter. A liquid medicine is placed in the atomizer and the inlet 31 is connected to a source of fresh gas such as air or oxygen-enriched air. The gas flows continuously during use at the rate of about six liters per minutes, and the medicine is aerosolized and flows into the wye 10.

The patient places the mouthpiece in his mouth and during inspiration the aerosol plus gas from the tubes are drawn through the mouthpiece and into the patient's respiratory system. Any additional or makeup gas required by the patient is room air which flows into the tubes through the filters 18 and 19, and this filtered air flows into the tubes and a portion through the mouthpiece 14 to the patient.

During expiration by the patient, the aerosol gas from the nebulizer 28 continues to flow into the wye, and this mixture of the aerosol gas plus the exhaled gas from the patient flows into the two tubes 16 and 17.

The mixture pushes any fresh gas ahead of it out of the tubes and some of the mixture may flow out through the filters, but, of course, the outflow is filtered to remove the medication and infectious matter.

Between breaths, the gas and medicine from the nebulizer continue to flow into the center of the wye; it flows into the two tubes 16 and 17 and pushes the exhaled gas mixture ahead of it and out through the filters. The aerosol is thus stored in the two tubes which serve as reservoirs for use by the patient during the next inspiratory portion of the breathing cycle.

In an alternative embodiment of the invention, one of the two filters 18 and 19 has a lesser weight (and a corresponding lower air flow resistance) than the other filter. For example, the filter 18 may have a weight of approximately 250 grams per square meter and the filter 19 may have a weight of approximately 150 grams per square meter. As a consequence of the different weights and flow resistance (or different air pressure drops), the gas flow is biased into the tube 17 having the lower weight filter.

During exhalation, a larger proportion of the exhaled gas flows out through the tube 17 and the filter 19, and the tube 17 will have a higher concentration of $CO_2$ than the leg 16. Between breaths, the aerosolized gas from the nebulizer flows into both tubes and expels the $CO_2$, but the $CO_2$ in the tube 17 will be purged more quickly and filled with fresh gas and aerosol. During inhalation, the patient receives fresh gas and aerosol from the nebulizer and from both legs, and more make-up air will flow through the tube 17 to the patient.

The applicant's arrangement has numerous advantages over prior art devices for the same purpose. Among these are:

1. Gas flow both into and out of the tubes is filtered.
2. There are no check valves, which in prior art devices add weight and expense and can require excessive inspiratory effort for a very sick patient.
3. The two tubes form parallel reservoirs for storage of aerosol, the reservoirs having a capacity greater than those of prior art devices.
4. The reservoir part of the device is compact, and the size of the reservoir can easily be increased by increasing the length of the tubes without adding significant bulk.
5. The use of filters instead of valves results in a device which has a simpler construction and a lower cost.
6. The device is compact and lightweight, and relatively easy to handle by a sick person.
7. The filters also operate as valves to maximize the total amount of aerosol delivered to a patient.
8. The location of the nebulizer 28 at the center of the wye enables the aerosol and fresh gas to flow into the two tubes and/or into the mouthpiece.

What is claimed is:

1. A nebulizer system comprising:
   a) a member forming first, second, third and fourth gas flow passages,
   b) first and second tubes, each of said tubes having first and second ends and said first ends being connected to said first and second passages, said first and second tubes and said first and second passages being valveless and gas being flowable both into and out of said second ends from ambient air,
   c) first and second filters mounted in said second ends of said tubes,
   d) means connected to said third passage and adapted to be connected to a patient and to carry gas to and from a patient, and
   e) a nebulizer connected to said fourth passage for feeding gas into said member.

2. A nebulizer system as set forth in claim 1, wherein said member is a wye, said first, second and third passages being substantially in one plane and said fourth passage extending substantially transversely of said first, second and third passages.

3. A nebulizer system as set forth in claim 1, wherein said fourth passage is substantially midway between said first, second and third passages.

4. A nebulizer system as set forth in claim 1, wherein said first and second filters have the same weight.

5. A nebulizer system as set forth in claim 1, wherein said first filter has a substantially lighter weight than said second filter.

6. A nebulizer system as set forth in claim 1, wherein said filters operate to filter out medicine, bacteria and virus in both directions of gas flow.

7. A nebulizer system comprising:
   a) a wye member having first, second and third substantially parallel gas flow passages,
   b) means connected to said third passage and adapted to conduct gases to and from a patient,
   c) a nebulizer having an outlet connected to substantially the center of said wye and substantially midway between said first, second and third passages for feeding gas into said first, second and third passages, and
   d) a filter connected to each of said first and second passages, said first and second passages being otherwise valveless and gas being flowable in both directions therethrough.

8. A nebulizer system as set forth in claim 7, wherein said first, second and third passages are substantially in one plane, and said outlet of said nebulizer is substantially transverse of said plane.

9. A nebulizer system as set forth in claim 7, and further comprising first and second tubes connected to said first and second passages, respectively, and said filters being mounted in said tubes.

10. A nebulizer system as set forth in claim 7, wherein said filters have substantially the same weight.

11. A nebulizer system as set forth in claim 7, wherein one of said filters has substantially less weight than the other of said filters.

* * * * *